(12) United States Patent
Belliotti et al.

(10) Patent No.: US 6,521,650 B1
(45) Date of Patent: Feb. 18, 2003

(54) AMINES AS PHARMACEUTICAL AGENTS

(75) Inventors: Thomas Richard Belliotti, Saline, MI (US); Justin Stephen Bryans, Balsham (GB); Thomas Capiris, Plymouth, MI (US); David Christopher Horwell, Cambridge (GB); Clare Octavia Kneen, Essex (GB); David Juergen Wustrow, Ann Arbor, MI (US)

(73) Assignee: Pfizer, Inc., Ann Arbor, MI (US)

( * ) Notice: Subject to any disclaimer, the term of this patent is extended or adjusted under 35 U.S.C. 154(b) by 0 days.

(21) Appl. No.: 09/509,917

(22) PCT Filed: Nov. 10, 1998

(86) PCT No.: PCT/US98/23917

§ 371 (c)(1),
(2), (4) Date: Apr. 4, 2000

(87) PCT Pub. No.: WO99/31074

PCT Pub. Date: Jun. 24, 1999

Related U.S. Application Data

(60) Provisional application No. 60/069,773, filed on Dec. 16, 1997, and provisional application No. 60/104,924, filed on Oct. 20, 1998.

(51) Int. Cl.$^7$ .............. C07D 257/04; A61K 31/41

(52) U.S. Cl. .............. 514/364; 514/360; 514/361; 514/381; 548/122; 548/129; 548/132; 548/254

(58) Field of Search ................. 548/122, 132, 548/129, 254; 514/364, 381, 360, 361

(56) References Cited

U.S. PATENT DOCUMENTS

| | | | |
|---|---|---|---|
| 4,024,175 A | 5/1977 | Satzinger et al. | 260/468 J |
| 4,087,544 A | 5/1978 | Satzinger et al. | 424/305 |
| 5,563,175 A | 10/1996 | Silverman et al. | 514/561 |
| 5,599,973 A | 2/1997 | Silverman et al. | 562/443 |
| 5,608,090 A | 3/1997 | Silverman et al. | 552/10 |
| 5,684,189 A | 11/1997 | Silverman et al. | 562/553 |
| 5,710,304 A | 1/1998 | Silverman et al. | 558/52 |
| 5,847,151 A | 12/1998 | Silverman et al. | 548/230 |
| 6,028,214 A | 2/2000 | Silverman et al. | 560/188 |

*Primary Examiner*—Robert Gerstl
(74) *Attorney, Agent, or Firm*—McDonnell Boehnen Hulbert & Berghoff

(57) ABSTRACT

Novel gamma aminobutyric acids of formula (I) are disclosed and are useful as agents in the treatment of epilepsy, faintness attacks, hypokinesia, cranial disorders, neurodegenerative disorders, depression, anxiety, panic, pain, neuropathological disorders, inflammation, and gastrointestinal damage. Processes for the preparation and intermediates useful in the preparation are also disclosed.

5 Claims, No Drawings

AMINES AS PHARMACEUTICAL AGENTS

This application claims benefit of Provisional Applications No. 60/069,773 filed Dec. 16, 1997 and No. 60/104,924 filed Oct. 20, 1998.

BACKGROUND OF THE INVENTION

Compounds of formula

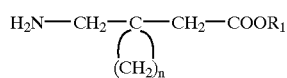

wherein $R_1$ is hydrogen or a lower alkyl radical and n is 4, 5, or 6 are known in U.S. Pat. No. 4,024,175 and its divisional U.S. Pat. No. 4,087,544. The uses disclosed are: protective effect against cramp induced by thiosemicarbazide; protective action against cardiazole cramp; the cerebral diseases, epilepsy, faintness attacks, hypokinesia, and cranial traumas; and improvement in cerebral functions. The compounds are useful in geriatric patients. The patents are hereby incorporated by reference.

Compounds of formula

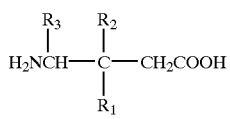

wherein $R_1$ is a straight or branched alkyl group having from 1 to 6 carbon atoms, phenyl, or cycloalkyl having from 3 to 6 carbon atoms; $R_2$ is hydrogen or methyl; and $R_3$ is hydrogen, methyl, or carboxyl are known in U.S. Pat. No. 5,563,175 and various divisionals. These patents are hereby incorporated by reference.

SUMMARY OF THE INVENTION

The compounds of the instant invention are novel amines and their pharmaceutically acceptable salts useful in a variety of disorders. The disorders include: epilepsy, faintness attacks, hypokinesia, cranial disorders, neurodegenerative disorders, depression, anxiety, panic, pain, neuropathological disorders, inflammation, and gastrointestinal disorders.

The compounds of the invention are those of formulas 1A and 1B below.

Preferred compounds are those of formulas 1A and 1B wherein R is a sulfonamide selected from —NHSO$_2$R$^{15}$ or —SO$_2$NHR$^{15}$ wherein R$^{15}$ is straight or branched alkyl or trifluoromethyl.

Especially preferred are:
4-Methyl-2-(1H-tetrazol-5-ylmethyl)-pentylamine;
3-(2-Aminomethyl-4-methyl-pentyl)-4H-[1,2,4]oxadiazole-5-thione, HCl;
3-(2-Aminomethyl-4-methyl-pentyl)-4H-[1,2,4]oxadiazole-5-one, HCl;
(2-Aminomethyl-4-methyl-pentyl)-phosphonic acid;
3-(3-Amino-2-cyclopentyl-propyl)-4H-[1,2,4]oxadiazol-5-one;
3-(3-Amino-2-cyclopentyl-propyl)-4H-[1,2,4]thiadiazol-5-one;
2-Cyclopentyl-3-(2-oxo-2,3-dihydro-2λ$^4$-[1,2,3,5]oxathiadiazol-4-yl)-propylamine;
3-(3-Amino-2-cyclobutyl-propyl)-4H-[1,2,4]oxadiazol-5-one;
3-(3-Amino-2-cyclobutyl-propyl)-4H-[1,2,4]thiadiazol-5-one; and
2-Cyclobutyl-3-(2-oxo-2,3-dihydro-2λ$^4$-[1,2,3,5]oxathiadiazol-4-yl)-propylamine.

Other preferred compounds are those of formulas 1A and 1B wherein R is a phosphonic acid, —PO$_3$H$_2$.

Other preferred compounds are those of Formulas 1A and 1B wherein

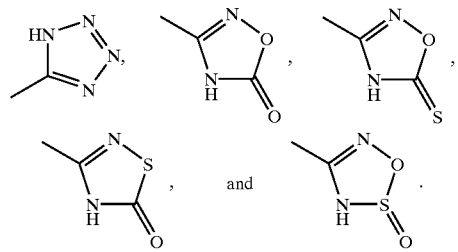

Especially preferred are:

DETAILED DESCRIPTION OF THE INVENTION

The amines of the instant invention are compounds of formula 1A and 1B and the pharmaceutically acceptable salts thereof.

The compounds of the invention are those of formula

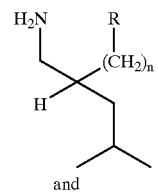

1A and

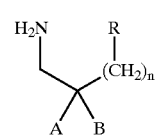

1B or a pharmaceutically acceptable salt thereof wherein:
n is an integer of from 0 to 2;
R is sulfonamide,
  amide,
  phosphonic acid,
  heterocycle,
  sulfonic acid, or
  hydroxamic acid;
A is hydrogen or methyl; and

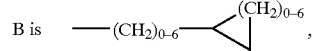

straight or branched alkyl of from 1 to 11 carbons, or —(CH$_2$)$_{1-4}$—Y—(CH$_2$)$_{0-4}$-phenyl wherein Y is —O—, —S—, —NR'$_3$ wherein R'$_3$ is alkyl of from 1 to 6 carbons, cycloalkyl of from 3 to 8 carbons, benzyl or phenyl wherein benzyl or phenyl can be unsubstituted or substituted with from 1 to 3 substituents each independently selected from alkyl, alkoxy, halogen, hydroxy, carboxy, carboalkoxy, trifluoromethyl, and nitro.

Since amino acids are amphoteric, pharmacologically compatible salts can be salts of appropriate inorganic or organic acids, for example, hydrochloric, sulphuric, phosphoric, acetic, oxalic, lactic, citric, malic, salicylic, malonic, maleic, succinic, methanesulfonic acid, and ascorbic. Starting from corresponding hydroxides or carbonates, salts with alkali metals or alkaline earth metals, for example, sodium, potassium, magnesium, or calcium are formed. Salts with quaternary ammonium ions can also be prepared with, for example, the tetramethyl-ammonium ion. The carboxyl group of the amino acids can be esterified by known means.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

The terms used to define the invention are as described below.

Sulfonamides are those of formula —NHSO$_2$R$^{15}$ or —SO$_2$NHR$^{15}$ wherein R$^{15}$ is a straight or branched alkyl group of from 1 to 6 carbons or a trifluoromethyl.

Amides are compounds of formula —NHCOR$^{12}$ wherein R$^{12}$ is straight or branched alkyl of from 1 to 6 carbons, benzyl, and phenyl.

Phosphonic acids are —PO$_3$H$_2$.

Sulfonic acids are —SO$_3$H.

Hydroxamic acid is

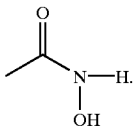

Heterocycles are groups of from 1 to 2 rings, with from 1 to 6 heteroatoms selected from oxygen, nitrogen, and sulfur.

Preferred heterocycles are

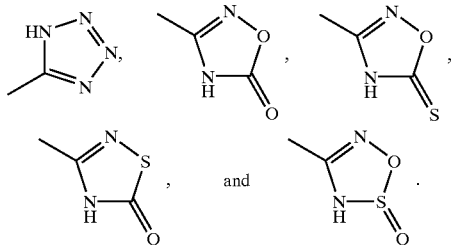

The term alkyl is a straight or branched group of from 1 to 11 carbon atoms including but not limited to methyl, ethyl, propyl, n-propyl, isopropyl, butyl, 2-butyl, tert-butyl, pentyl, hexyl, and n-hexyl, heptyl, octyl, nonyl, decyl, and undecyl except as where otherwise stated.

The cycloalkyl groups are from 3 to 8 carbons and are cyclopropyl, cyclobutyl, cyclopentyl, cyclohexyl, cycloheptyl, and cyclooctyl unless otherwise stated.

The benzyl and phenyl groups may be unsubstituted or substituted by from 1 to 3 substituents selected from hydroxy, carboxy, carboalkoxy, halogen, CF$_3$, nitro, alkyl, and alkoxy. Preferred are halogens.

Alkoxy is as defined above for alkyl.

Halogen is fluorine, chlorine, and bromine and preferred are fluorine and chlorine.

Carboalkoxy is —COOalkyl wherein alkyl is as described above. Preferred are carbomethoxy and carboethoxy.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

Certain of the compounds of the present invention possess one or more chiral centers and each center may exist in the R(D) or S(L) configuration. The present invention includes all enantiomeric and epimeric forms as well as the appropriate mixtures thereof.

The radioligand binding assay using [$^3$H]gabapentin and the α$_2$δ subunit derived from porcine brain tissue was used ("The Novel Anti-convulsant Drug, Gabapentin, Binds to the a α$_2$δ Subunit of a Calcium Channel", Gee N. S., et al., *J. Biol Chem*, 1996;271(10):5768–5776).

The compounds of the invention show good binding affinity to the α$_2$δ subunit. Gabapentin (Neurontin®) is about 0.10 to 0.12 μM in this assay. Since the compounds of the instant invention also bind to the subunit, they are expected to exhibit pharmacologic properties comparable to gabapentin. For example, as agents for convulsions, anxiety, and pain.

TABLE 1

| R | α2δ Assay IC$_{50}$ (μM) | Pain Model % MPE 1 Hr | Pain Model % MPE 2 Hr | Vogel Conflict % of CI-1008 | DBA2 % Protection 1 Hr | DBA2 % Protection 2 Hr |
|---|---|---|---|---|---|---|
| (tetrazole) | 2.47 | 0 | 0 | 0.0 | 0 | 0 |
| (oxadiazole-thione) | >10 | | | | 0 | 0 |
| (oxadiazolone) | 1.52 | | | | | |
| PO$_3$H$_2$ | >10 | | | | 0 | 0 |

The compounds of the invention are related to Neurontin®, a marketed drug effective in the treatment of epilepsy. Neurontin® is 1-(aminomethyl)-cyclohexaneacetic acid of structural formula

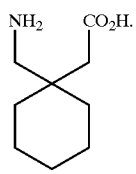

Preferred novel gabapentin and isobutyl-GABA analogs, their derivatives, and pharmaceutically acceptable salts are useful in the treatment of a variety of disorders including epilepsy, faintness attacks, hypokinesia, cranial disorders, neurodegenerative disorders, depression, anxiety, panic, pain, and neuropathological disorders. The compounds are of the general formula:

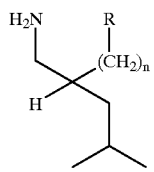

a pharmaceutically acceptable salt thereof or a prodrug thereof, where n=0,1,2, m=0,1,2,3, and R can be sulfonamides of the general formula —NHSO$_2$R$^1$ or —SO$_2$NHR$^1$ where R$^1$ is H or C$_1$–C$_4$ straight or branched chain alkyl or trifluoromethyl. R may also be an amide of the general formula —NHCOR$^1$. Or R may also be a phosphonic acid —PO$_3$H$_2$ (Lipinski C. A., *Ann. Rep. Med. Chem.*, 21:283 (1986)).

The compounds of the invention are also expected to be useful in the treatment of epilepsy.

The present invention also relates to therapeutic use of the compounds of the mimetic as agents for neurodegenerative disorders.

Such neurodegenerative disorders are, for example, Alzheimer's disease, Huntington's disease, Parkinson's disease, Amyotrophic Lateral Sclerosis, and epilepsy.

The present invention also covers treating neurodegenerative disorders termed acute brain injury. These include but are not limited to: stroke, head trauma, and asphyxia.

Stroke refers to a cerebral vascular disease and may also be referred to as a cerebral vascular incident (CVA) and includes acute thromboembolic stroke. Stroke includes both focal and global ischemia. Also, included are transient cerebral ischemic attacks and other cerebral vascular problems accompanied by cerebral ischemia such as in a patient undergoing carotid endarterectomy specifically or other cerebrovascular or vascular surgical procedures in general, or diagnostic vascular procedures including cerebral angiography and the like.

Pain refers to acute as well as chronic pain.

Acute pain is usually short-lived and is associated with hyperactivity of the sympathetic nervous system. Examples are postoperative pain and allodynia.

Chronic pain is usually defined as pain persisting from 3 to 6 months and includes somatogenic pains and psychogenic pains. Other pain is nociceptive.

Still other pain is caused by injury or infection of peripheral sensory nerves. It includes, but is not limited to pain from peripheral nerve trauma, herpes virus infection, diabetes mellitus, causalgia, plexus avulsion, neuroma, limb amputation, and vasculitis. Neuropathic pain is also caused by nerve damage from chronic alcoholism, human immunodeficiency virus infection, hypothyroidism, uremia, or vitamin deficiencies. Neuropathic pain includes, but is not limited to pain caused by nerve injury such as, for example, the pain diabetics suffer from.

Psychogenic pain is that which occurs without an organic origin such as low back pain, atypical facial pain, and chronic headache.

Other types of pain are: inflammatory pain, osteoarthritic pain, trigeminal neuralgia, cancer pain, diabetic neuropathy, restless leg syndrome, acute herpetic and postherpetic neuralgia, causalgia, brachial plexus avulsion, occipital neuralgia, gout, phantom limb, burn, and other forms of neuralgia, neuropathic and idiopathic pain syndrome.

Other incidents are head trauma, spinal cord trauma, or injury from general anoxia, hypoxia, hypoglycemia, and hypotension as well as similar injuries seen during procedures from embole, hyperfusion, and hypoxia.

The instant invention would be useful in a range of incidents, for example, during cardiac bypass surgery, in incidents of intracranial hemorrhage, in perinatal asphyxia, in cardiac arrest, and status epilepticus.

A skilled physician will be able to determine the appropriate situation in which subjects are susceptible to or at risk of, for example, stroke as well as suffering from stroke for administration by methods of the present invention.

The compounds of the invention are also expected to be useful in the treatment of depression. Depression can be the result of organic disease, secondary to stress associated with personal loss, or idiopathic in origin. There is a strong tendency for familial occurrence of some forms of depression suggesting a mechanistic cause for at least some forms of depression. The diagnosis of depression is made primarily by quantification of alterations in patients' mood. These evaluations of mood are generally performed by a physician or quantified by a neuropsychologist using validated rating scales, such as the Hamilton Depression Rating Scale or the Brief Psychiatric Rating Scale. Numerous other scales have been developed to quantify and measure the degree of mood alterations in patients with depression, such as insomnia, difficulty with concentration, lack of energy, feelings of worthlessness, and guilt. The standards for diagnosis of depression as well as all psychiatric diagnoses are collected in the Diagnostic and Statistical Manual of Mental Disorders (Fourth Edition) referred to as the DSM-IV-R manual published by the American Psychiatric Association, 1994.

GABA is an inhibitory neurotransmitter with the central nervous system. Within the general context of inhibition, it seems likely that GABA-mimetics might decrease or inhibit cerebral function and might therefore slow function and decrease mood leading to depression.

The compounds of the instant invention may produce an anticonvulsant effect through the increase of newly created GABA at the synaptic junction. If gabapentin does indeed increase GABA levels or the effectiveness of GABA at the synaptic junction, then it could be classified as a GABA-mimetic and might decrease or inhibit cerebral function and might, therefore, slow function and decrease mood leading to depression.

The compounds of the invention will be useful in the treatment of gastrointestinal disorders, especially irritable bowel syndrome.

The fact that a GABA agonist or GABA-mimetic might work just the opposite way by increasing mood and thus, be an antidepressant, is a new concept, different from the prevailing opinion of GABA activity heretofore.

The compounds of the instant invention are also expected to be useful in the treatment of anxiety and of panic as demonstrated by means of standard pharmacological procedures.

MATERIAL AND METHODS

Carrageenin-Induced Hyperalgesia

Nociceptive pressure thresholds were measured in the rat paw pressure test using an analgesymeter (Randall-Sellitto Method: Randall L. O., Sellitto J. J., A method for measurement of analgesic activity on inflamed tissue. *Arch. Int. Pharmacodyn.*, 4:409–419 (1957)). Male Sprague-Dawley rats (70–90 g) were trained on this apparatus before the test day. Pressure was gradually applied to the hind paw of each rat and nociceptive thresholds were determined as the pressure (g) required to elicit paw withdrawal. A cutoff point of 250 g was used to prevent any tissue damage to the paw. On the test day, two to three baseline measurements were taken before animals were administered 100 μL of 2% carrageenin by intraplantar injection into the right hind paw. Nociceptive thresholds were taken again 3 hours after carrageenin to establish that animals were exhibiting hyperalgesia. Animals were dosed with either gabapentin (3–300 mg/kg, s.c.), morphine (3 mg/kg, s.c.), or saline at 3.5 hours after carrageenin and nociceptive thresholds were examined at 4, 4.5, and 5 hours post carrageenin.

Semicarbazide-Induced Tonic Seizures

Tonic seizures in mice are induced by subcutaneous administration of semicarbazide (750 mg/kg). The latency to the tonic extension of forepaws is noted. Any mice not convulsing within 2.0 hours after semicarbazide are considered protected and given a maximum latency score of 120 minutes.

Animals

Male Hooded Lister rats (200–250 g) are obtained from Interfauna (Huntingdon, UK) and male TO mice (20–25 g) are obtained from Bantin and Kingman (Hull, UK). Both rodent species are housed in groups of six. Ten Common Marmosets (Callithrix Jacchus) weighing between 280 and 360 g, bred at Manchester University Medical School (Manchester, UK) are housed in pairs. All animals are housed under a 12-hour light/dark cycle (lights on at 07.00 hour) and with food and water ad libitum.

Drug Administration

Drugs are administered either intraperitoneally (IP) or subcutaneously (SC) 40 minutes before the test in a volume of 1 mL/kg for rats and marmosets and 10 mL/kg for mice.

Mouse Light/Dark Box

The apparatus is an open-topped box, 45 cm long, 27 cm wide, and 27 cm high, divided into a small (2/5) and a large (3/5) area by a partition that extended 20 cm above the walls (Costall B., et al., Exploration of mice in a black and white box: validation as a model of anxiety. *Pharmacol. Biochem. Behav.*, 32:777–785 (1989)).

There is a 7.5×7.5 cm opening in the center of the partition at floor level. The small compartment is painted black and the large compartment white. The white compartment is illuminated by a 60-W tungsten bulb. The laboratory is illuminated by red light. Each mouse is tested by placing it in the center of the white area and allowing it to explore the novel environment for 5 minutes. The time spent in the illuminated side is measured (Kilfoil T., et al., Effects of anxiolytic and anxiogenic drugs on exploratory activity in a simple model of anxiety in mice. *Neuropharmacol.*, 28:901–905 (1989)).

Rat Elevated X-Maze

A standard elevated X-maze (Handley S. L., et al., Effects of alpha-adrenoceptor agonists and antagonists in a maze-exploration model of 'fear'-motivated behavior. *Naunyn-Schiedeberg's Arch. Pharmacol.*, 327:1–5 (1984)), was automated as previously described (Field, et al., Automation of the rat elevated X-maze test of anxiety. *Br. J. Pharmacol.*, 102(Suppl):304P (1991)). The animals are placed on the center of the X-maze facing one of the open arms. For determining anxiolytic effects the entries and time spent on the end half sections of the open arms is measured during the 5-minute test period (Costall, et al., Use of the elevated plus maze to assess anxiolytic potential in the rat. *Br. J. Pharmacol.*, 96(Suppl):312P (1989)).

Marmoset Human Threat Test

The total number of body postures exhibited by the animal towards the threat stimulus (a human standing approximately 0.5 m away from the marmoset cage and staring into the eyes of the marmoset) is recorded during the 2-minute test period. The body postures scored are slit stares, tail postures, scent marking of the cage/perches, piloerection, retreats, and arching of the back. Each animal is exposed to the threat stimulus twice on the test day before and after drug treatment. The difference between the two scores is analyzed using one-way analysis of variance followed by Dunnett's t-test. All drug treatments are carried out SC at least 2 hours after the first (control) threat. The pretreatment time for each compound is 40 minutes.

Rat Conflict Test

Rats are trained to press levers for food reward in operant chambers. The schedule consists of alternations of four 4-minute unpunished periods on variable interval of 30 seconds signaled by chamber lights on and three 3-minute punished periods on fixed ratio 5 (by footshock concomitant to food delivery) signaled by chamber lights off. The degree of footshock is adjusted for each rat to obtain approximately 80% to 90% suppression of responding in comparison with unpunished responding. Rats receive saline vehicle on training days.

The compounds of the instant invention are also expected to be useful in the treatment of pain and phobic disorders (*Am. J. Pain Manag.*, 5:7–9 (1995)).

The compounds of the instant invention are also expected to be useful in treating the symptoms of manic, acute or chronic, single upside, or recurring depression. They are also expected to be useful in treating and/or preventing bipolar disorder (U.S. Pat. No. 5,510,381).

TNBS-Induced Chronic Visceral Allodynia In Rats

Injections of trinitrobenzene sulfonic (TNBS) into the colon have been found to induce chronic colitis. In human, digestive disorders are often associated with visceral pain. In these pathologies, the visceral pain threshold is decreased indicating a visceral hypersensitivity. Consequently, this study was designed to evaluate the effect of injection of TNBS into the colon on visceral pain threshold in a experimental model of colonic distension.

Animals and Surgery

Male Sprague-Dawley rats (Janvier, Le Genest-St-Ilse, France) weighing 340–400 g are used. The animals are housed 3 per cage in a regulated environment (20±1° C., 50±5% humidity, with light 8:00 am to 8:00 pm). Under anesthesia (ketamine 80 mg/kg ip; acepromazin 12 mg/kg ip), the injection of TNBS (50 mg/kg) or saline (1.5 mL/kg) is performed into the proximal colon (1 cm from the cecum). After the surgery, animals are individually housed in polypropylene cages and kept in a regulated environment (20±1° C., 50±5% humidity, with light 8:00 am to 8:00 pm) during 7 days.

Experimental Procedure

At Day 7 after TNBS administration, a balloon (5–6 cm length) is inserted by anus and kept in position (tip of balloon 5 cm from the anus) by taping the catheter to the base of the tail. The balloon is progressively inflated by step of 5 mm Hg, from 0 to 75 mm Hg, each step of inflation lasting 30 seconds. Each cycle of colonic distension is controlled by a standard barostat (ABS, St-Dié, France). The threshold corresponds to the pressure which produced the first abdominal contraction and the cycle of distension is then discontinued. The colonic threshold (pressure expressed in mm Hg) is determined after performance of four cycles of distension on the same animal.

Determination of the Activity of the Compound

Data is analyzed by comparing test compound-treated group with TNBS-treated group and control group. Mean and sem are calculated for each group. The antiallodynic activity of the compound is calculated as follows:

Activity (%)=(group C—group T)/(group A—group T)
    Group C: mean of the colonic threshold in the control group
    Group T: mean of the colonic threshold in the TNBS-treated group
    Group A: mean of the colonic threshold in the test compound-treated group Statistical Analysis Statistical significance between each group was determined by using a one-way ANOVA followed by Student's unpaired t-test. Differences were considered statistically significant at $p<0.05$.

Compounds

TNBS is dissolved in EtOH 30% and injected under a volume of 0.5 mL/rat. TNBS is purchased from Fluka.

Oral administration of the test compound or its vehicle is performed 1 hour before the colonic distension cycle.

Sub-cutaneous administration of the test compound or its vehicle is performed 30 minutes before the colonic distension cycle.

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either a compound of Formula I or a corresponding pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection liquid preparations can be formulated in solution in aqueous polyethylene glycol solution.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 1 g according to the particular application and the potency of the active component. In medical use the drug may be administered three times daily as, for example, capsules of 100 or 300 mg. The composition can, if desired, also contain other compatible therapeutic agents.

In therapeutic use, the compounds utilized in the pharmaceutical method of this invention are administered at the initial dosage of about 0.01 mg to about 100 mg/kg daily. A daily dose range of about 0.01 mg to about 100 mg/kg is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

R may also be a heterocycle such as tetrazole

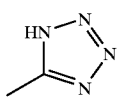

or other heterocycles which have been used as replacements for $CO_2H$, such as

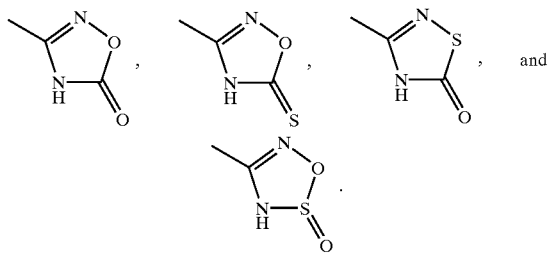

(Kohara Y., Kubo K., Imamiya E., Wada T., Inada Y., and Naka T., *J. Med. Chem.*, 39:5228 (1996)).

Sulfonic and hydroxamic acids are also preferred. Tetrazoles of Formula 1A can be synthesized by the route outlined in Scheme 1

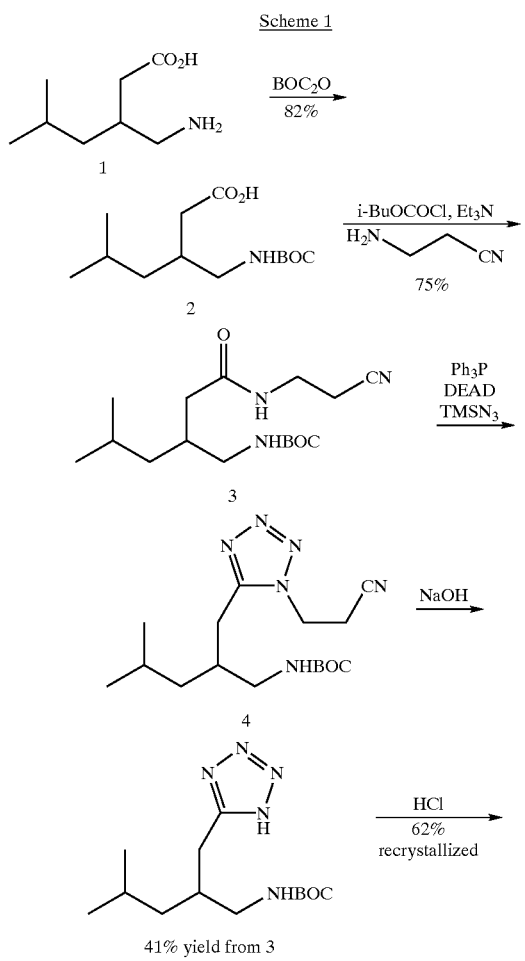

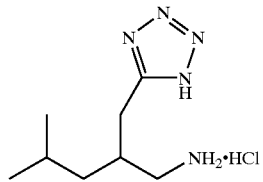

The following examples are illustrative of the instant invention; they are not intended to limit the scope.

EXAMPLE 1

4-Methyl-2-(1H-tetrazol-5-ylmethyl)-pentylamine

Compound 3 in Scheme 1 {2-[(2-Cyano-ethylcarbamoyl)-methyl]-4-methyl-pentyl}-carbamic acid tert-butyl ester A solution of compound 2 (8.0 g, 0.03 mol) (prepared in the usual manner from $(BOC)_2$ and pregabalin) was taken up in 250 mL dry THF and cooled in an ice water bath. Triethyl amine (4.62 mL, 0.033 mol) was added followed by the addition of isobutyle chloroformate (4 mL, 0.031 mol). The reaction was stirred at 0° C. for about 15 minutes during which time a precipitate formed. In a separate flask was placed 3-aminoproprionitrile fumarate (3.95 g, 0.03 mol) in 35 mL of 1 M NaOH and 300 mL of THF. This mixture was cooled to 0° C. and treated with the mixed anhydride formed above in four portions. Before each portion was added, 35 mL of 1 M NaOH was added to the mixture. The reaction was stirred for 24 hours and was then concentrated to remove THF. The resulting aqueous was extracted with three times ethyl acetate. The combined organic extracts were washed with brine, dried over magnesium sulfate. The solvents were removed under reduced pressure to give 6.6 g green oil. MS(APCI) m/z 312 (M+1).

Compound 4 in Scheme 1 [4-Methyl-2-(1-(2-cyano-ethyl)-tetrazol-5-ylmethyl)-pentyl]-carbamic acid tert-butyl ester and compound 5 [4-Methyl-2-(1H-tetrazol-5-ylmethyl)-pentyl]-carbamic acid tert-butyl ester The cyanoamide (6.5 g, 0.0209 mol) and triphenylphosphine (11.06 g, 0.042 mol) were dissolved in 300 mL of dry THF. The solution was treated with DEAD (6.7 mL, 0.0425 mol) and $TMSN_3$ (5.75 mL, 0.043 mol). The reaction was stirred for 24 hours, and the reaction mixture was cooled to 0° C. and treated with 900 mL of an aqueous solution containing 46.9 g of $(NH_4)_2Ce(IV)NO_3$. The reaction mixture was concentrated to remove THF and extracted with three portions of $CH_2Cl_2$. The combined organic layers were dried with brine and $Na_2SO_4$ and the solvents were removed under reduced pressure to give a clear oil which was passed through a plug of silicagel to give the product admixed with triphenylphospine oxide. This crude mixture was dissolved in 200 mL THF and 50 mL of 2N NaOH. The mixture was heated to reflux for 2 hours then stirred at room temperature overnight. The THF was removed under reduced pressure and the resulting residue diluted with water. After extraction with ether, the aqueous phase was acidified to pH 7 and extracted with 21 mL of 4N HCl. The aqueous phase was then saturated with solid $KH_2PO_4$. The aqueous mixture was extracted with $CH_2Cl_2$. The organic extracts were washed with brine and dried over $Na_2SO_4$. Evaporation of the organic solvents under reduced pressure resulted in isolation of 3.4 g of an amber oil.

4-Methyl-2-(1H-tetrazol-5-ylmethyl)-pentylamine

The material from the previous step (0.9 g, 3.18 mmol) was taken up in 20 mL of 4 M HCl in dioxane. The reaction was allowed to stand for 1 hour. A solid formed, 10 mL of ether was added, and the reaction was filtered to give 780 mg white solid. MS(APCI) m/z 184 (M+1).

EXAMPLE 2

IsobutylGABA oxadiazolonethione (G) is also named 3-(2-Aminomethyl-4-methyl-pentyl)-4H-[1,2,4]oxadiazole-5-thione; HCl

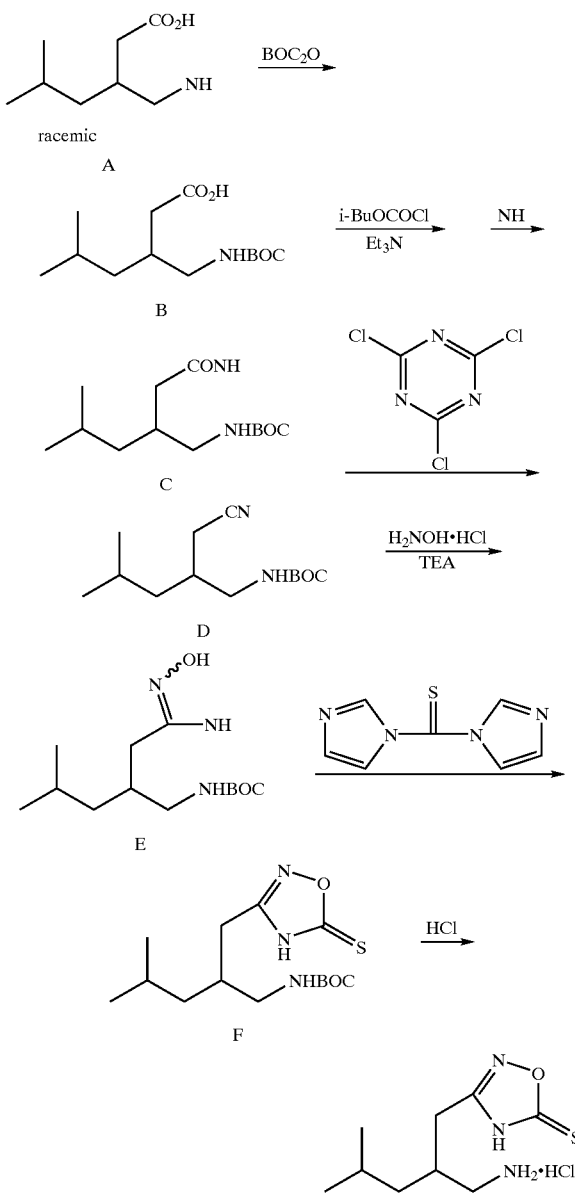

BOC-IsobutylGABA (B)

A solution of di-tert-butyl dicarbonate (13.1 g, 0.06 mol) in THF (200 mL) was added, over a 10-minute period, to a solution of isobutylGABA (9.95 g, 0.056 mol) in 1N NaOH (125 mL) and THF (50 mL) cooled in an ice-water bath. The reaction mixture was stirred at room temperature 3 hours, concentrated to remove THF, saturated with saturated $KH_2PO_4$ and extracted 3×EtOAc. The extracts were washed 2×brine, dried over $MgSO_4$, and evaporated to yield 13.8 g (95%) of a white solid, mp 84–88° C. MS (APCI) m/z 260 (M+1).

BOC-IsobutylGABA amide (C)

A solution of BOC-IsobutylGABA (6.78 g, 0.026 mol) and triethyl amine (3.0 g, 0.030 mol) was cooled to 0° C. and isobutyl chloroformate (3.9 g, 0.029 mol) was slowly added. After stirring 20 minutes at 0° C., ammonia gas was bubbled into the reaction mixture for 30 minutes, and then the mixture was stirred at room temperature 18 hours. The mixture was concentrated to remove THF, suspended in water, and extracted 3×EtOAc. The extracts were washed 1×10% $Na_2CO_3$, 2×brine, and dried over $Na_2SO_4$. Evaporation yielded 4.9 g (73%) of an oil which was used without further purification. MS (APCI) m/z 259 (M+1).

BOC-IsobutylGABA nitrile (D)

A solution of BOC-IsobutylGABA amide (4.6 g, 0.0178 mol) in DMF (15 mL) was added, all at once, to cyanuric chloride (1.66 g, 0.009 mol) and stirred 30 minutes at room temperature. The reaction mixture was poured into a cold solution of $NaHCO_3$ (4.2 g, 0.05 mol) in water (150 mL). Solid $K_2CO_3$ was added to bring the pH to 9 and the mixture was extracted 2×$CH_2Cl_2$, washed 1×brine, and dried over $Na_2SO_4$. Evaporation yielded an oil, which was filtered through silica gel, eluting with $CH_2Cl_2$-EtOAc which yielded 3.8 g oil (89%), which was used without further purification. MS (APCI) m/z 240 (M), 239 (M−1); IR (Film) 2215 cm$^{-1}$.

BOC-IsobutylGABA amidoxime (E)

A solution of hydroxylamine was prepared by adding triethylamine (7.62 g, 0.075 mol) to a suspension of hydroxylamine hydrochloride (5.21 g, 0.075 mol) in DMSO (25 mL). After 15 minutes, the triethylamine hydrochloride was filtered off, and BOC-IsobutylGABA nitrile (3.61 g, 0.015 mol) was added to the filtrate. The mixture was heated at 75° C. for 17 hours. The mixture was diluted with water and extracted 3×EtOAc. The extracts were washed 2×brine, dried over $Na_2SO_4$, and evaporated to give an oil which was filtered through a short silica gel column, eluting with $CH_2Cl_2$-EtOAc to give 3.2 g (78%) oil. $^1$H NMR (CDCl$_3$) δ0.84 (d, 6H, J=6.35 Hz), 1.11 (m, 2H), 1.40 (s, 9H), 1.63 (m, 1H), 3.05 (m, 1H), 3.15 (m, 1H), 4.85 (m, 1H), 5.43 (m 1H); MS (APCI) 274 (M+1).

BOC-IsobutylGABA oxadiazolonethione (F)

A solution containing BOC-Isobutyl GABA amidoxime (0.5 g, 0.00183 mol), DBU (1.12 g, 0.00736 mol) and 90% 1,1'-thiocarbonyldiimidazole (0.398 g, 0.002 mol) in MeCN (12 mL) was stirred at room temperature 16 hours. The reaction mixture was evaporated to dryness, taken up in EtOAc, and washed with $KHSO_4$ solution. The EtOAc layer was extracted with 1N NaOH (100 mL). The alkaline extract was washed with Et$_2$O and acidified with saturated $KH_2PO_4$ and extracted 3×EtOAc. The extracts were washed 1×water, 1×brine and dried over $MgSO_4$. Evaporation yielded an oil, 0.25 g(43%). $^1$H NMR (CDCl$_3$) δ0.84 (d, 6H, J=6.59 Hz), 1.1 (m, 2H), 1.41 (s, 9H), 1.65 (m, 1H), 1.85 (m, 1H), 2.60 (m, 2H), 3.1 (m, 2H), 4.94 (m, 1H), 12.8 (s, 1H). MS (APCI) 316 (M+1).

IsobutylGABA oxadiazolonethione (G) is also named 3-(2-Aminomethyl-4-methyl-pentyl)4H-[1,2,4]oxadiazole-5-thione; HCl BOC-IsobutylGABA oxadiazolonethione (0.25 g, 0.79 mmol) was taken up in 4 M HCl in dioxane (10 mL) at room temperature for 1 hour. Evaporation followed by recrystallization of the residue from MeCN yielded cream-colored crystals, 0.108 g, mp 183–185° C. $^1$H NMR (DMSO-$d_6$) δ0.84 (d, 6H, J=6.59 Hz), 1.1 (m, 2H), 1.41 (s, 9H), 1.65 (m, 1H), 0.80 (d, 6H, J=6.59 Hz), 1.06 (m, 1H), 1.25 (m, 1H), 1.55 (m, 1H), 2.1 (m, 1H), 2.7 (m, 4H), 7.95 (s, 3H); MS (APCI) 216 (M+1). Anal. Calcd for $C_9H_{17}N_3OS \cdot HCl$: C, 42.93; H, 7.21; N, 16.69; Cl, 14.08. Found: C, 43.38; H, 7.24; N, 16.29; Cl, 14.17.

EXAMPLE 3

IsobutylGABA oxadiazolone (J) is also named 3-(2-Aminomethyl-4-methyl-pentyl)-4H-[1,2,4]oxadiazole-5-one; HCl

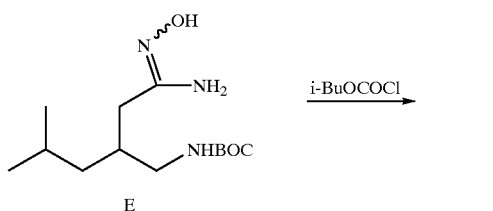

E

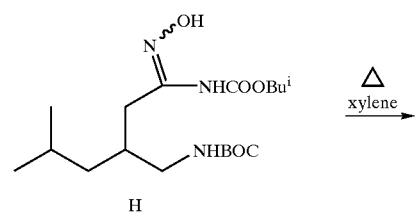

H

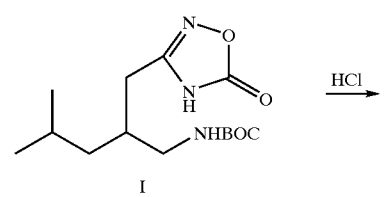

I

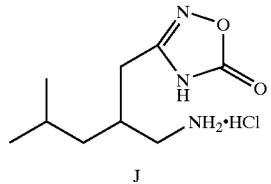

J

BOC-IsobutylGABA amidoxime carbamate (H)

Isobutyl chloroformate (0.253 g, 0.00185 mol) was added dropwise to a solution of BOC-IsobutylGABA amidoxime (0.5 g, 0.00183 mol) and pyridine (0.158 g, 0.002 mol) in DMF (10 ml) at 0° C. After 30 minutes at that temperature, the reaction mixture was diluted with water and extracted 3×EtOAc. The extracts were washed 1×water, 1×brine and dried over $MgSO_4$. Evaporation yielded an oil, 0.7 g (100%) which was used without further purification. MS (APCI) m/z 374 (M+1).

BOC-IsobutylGABA oxadiazolone (I)

BOC-IsobutylGABA amidoxime carbamate (0.7 g, 0.00183 mol) was taken up in xylene (20 mL) and heated under reflux 2 hours. Evaporation yielded a dark glassy oil which was taken up in $Et_2O$ and extracted with 1N NaOH. The alkaline phase was acidified with saturated $KH_2PO_4$ and extracted 3×EtOAc. The extracts were washed with brine, dried over $MgSO_4$ and evaporated to yield a brown oil, 0.25 g (46%), which was used without further purification. MS (APCI) m/z 300 (M+1).

IsobutylGABA oxadiazolone (J) is also named 3-(2-Aminomethyl-4-methyl-pentyl)-4H-[1,2,4]oxadiazole-5-one; HCl BOC-IsobutylGABA oxadiazolone(0.25 g, 0.835 mmol) was taken up in 4 M HCl in dioxane and allowed to stand 2.5 hours Evaporation followed by recrystallization of the residue from MeCN-$Et_2O$ yielded a tan solid, 53 mg (27%), mp 181–184° C. $^1$H NMR (DMSO-$d_6$) δ0.80 (d, 6H, J=6.35 Hz), 1.1 (m, 2H), 1.25 (s, 9H), 1.60 (m, 1H), 2.10 (m, 1H), 2.5–2.8 (m, 4H), 7.95 (s, 3), 12.39 (s, 1H). MS (APCI) 216 (M+1). Anal. Calcd for $C_9H_{17}N_3O_2 \cdot HCl$: C, 45.86; H, 7.70; N, 17.83; Cl, 15.04. Found: C, 45.40; H, 7.55; N, 16.79; Cl, 15.81.

EXAMPLE 4

Preparation of (2-Aminomethyl-4-methyl-pentyl)-phosphonic acid (9)

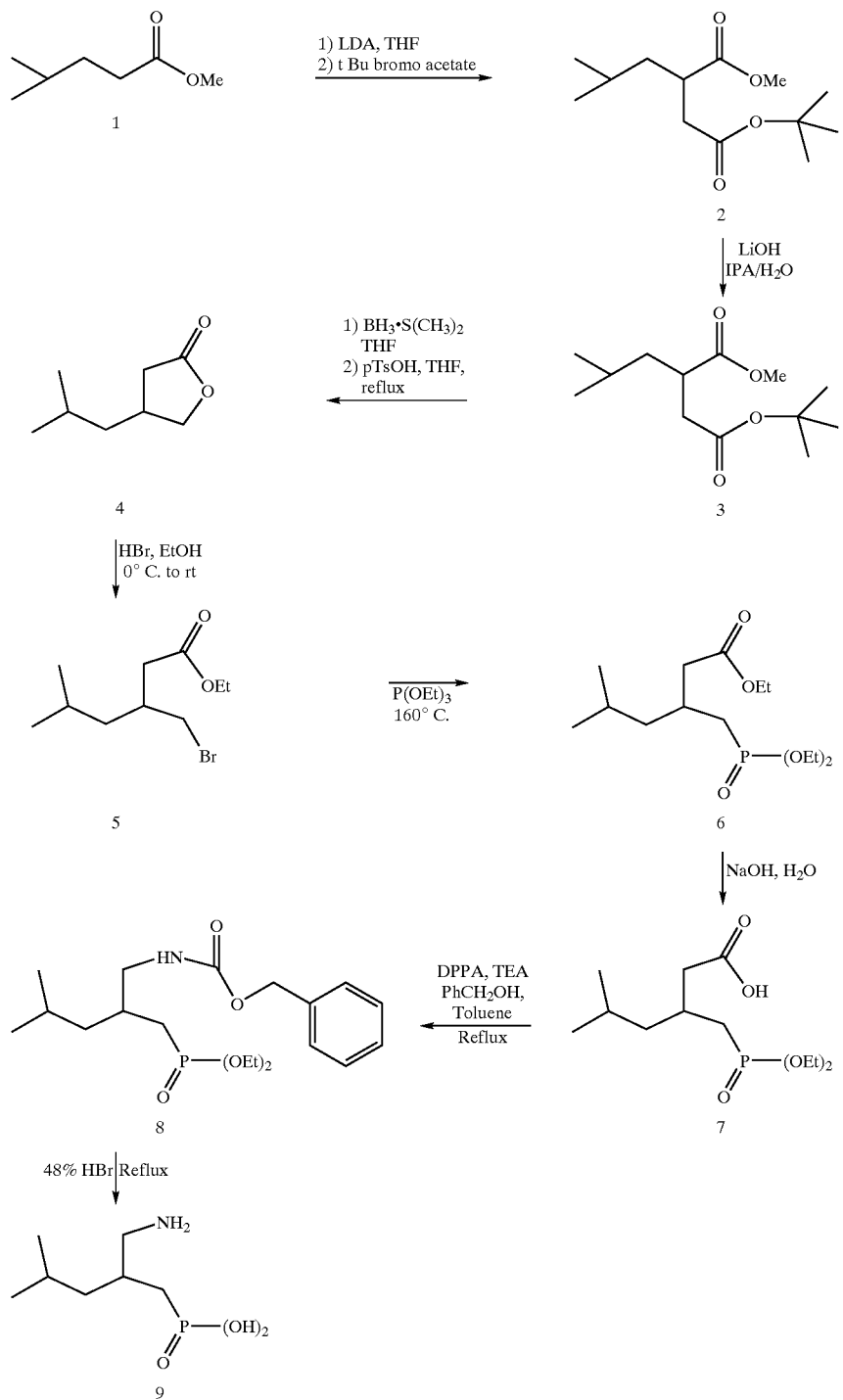

1. Preparation of 2-Isobutyl-succinic acid-4-t-butyl eser-1-methyl ester (2): 4-methylpentanoic acid methyl ester (10.0 g, 76.8 mmol) is added to a solution of LDA in 150 mL of THF at −78° C. under Ar. After 15 minutes, the anion solution is added by cannula to a solution of t-butyl bromoacetate (22.5 g, 115.2 mmol) in 50 mL of THF at −78° C., and the solution is stirred for 45 minutes. The reaction mixture is then warmed to room temperature, and treated with 100 mL of saturated $KH_2PO_4$. The THF is evaporated, and the organics are extracted into $Et_2O$ (3×50 mL). The $Et_2O$ is washed with 10% $Na_2S_2O_3$ and dried with $MgSO_4$. The solvent is evaporated, and the remaining oil is distilled under vacuum (0.1 mm Hg) to give 11.1 g (59% yield) of 2-isobutyl-succinic acid4-t-butyl ester-1-methyl ester boiling at 65° C. to 72° C. NMR ($H^1$, 400 MHz, $CDCl_3$) δ0.9 (6H, m); δ1.2 (1H, m); δ1.4 (9H, s); δ1.5 (2H, m); δ2.3 (1H, dd); δ2.5 (1H, dd); δ2.8 (1H, m); δ3.6 (3H, s).

2. Preparation of 2-Isobutyl-succinic acid-4-t-butyl ester (3): 2-isobutyl-succinic acid-4-t-butyl ester-1-methyl ester (11.1 g, 45.4 mmol) and $LiOH·H_2O$ (2.0 g, 47.7 mmol) are stirred in 180 mL of 3:1 IPA/H$_2$O at room temperature overnight. The reaction mixture is extracted with Et$_2$O (3×25 mL). The aqueous phase is acidified to pH=4, with saturated KH$_2$PO$_4$ and extracted with Et$_2$O (3×50 mL). The Et$_2$O is dried over MgSO$_4$, and evaporated to give 8.0 g (77% yield) of 2-isobutyl-succinic acid-4-t-butyl ester as an oil. NMR (H$^1$, 400 MHz, CDCl$_3$) δ0.9 (6H, m); δ1.3 (1H, m); δ1.4 (9H, s); δ1.6 (2H, m); δ2.3 (1H, dd); δ2.6 (1H, dd); δ2.8 (1H, m).

3. Preparation of 4-Isobutyl-dihydro-furan-2-one (4): A solution of 2-isobutyl-succinic acid-4-t-butyl ester (8.0 g, 34.7 mmol) in 100 mL of THF is cooled to 0° C. under Ar and borane dimethyl sulphide complex (2.6 g, 34.7 mmol) is added. The reaction mixture is stirred at 0° C. for 10 minutes, and at room temperature overnight. The solution is cooled to 0° C. and 100 mL of MeOH is added. The solvents are evaporated, and the remaining oil is dried under hi-vacuum for 2 hrs. The oil remaining is taken up in 100 mL of THF, and a catalytic amount of p-toluene sulfonic acid is added. The solution is warmed to reflux overnight. After being cooled to room temperature, the solvent is evaporated, and the oil is taken up in Et$_2$O (100 mL). The Et$_2$O solution is extracted with 2.0N Na$_2$CO$_3$ (2×50 mL) followed by 100 mL of brine and dried over MgSO$_4$. Evaporation of Et$_2$O followed by medium pressure chromatography (MPLC) of the remaining oil in 20% EtOAc/Hexanes gives 4.4 g (89% yield) of 4-isopropyl-dihydro-furan-2-one as an oil. NMR (H$^1$, 400 MHz, CDCl$_3$) δ0.9 (6H, m); δ1.3 (2H, dd); δ1.5 (1H, m); δ2.1 (1H, m); δ2.6 (2H, m); δ3.6 (1H, m); δ4.4 (1H, m).

4. Preparation of 3-Bromomethyl-3-isobutyl-propionic acid ethyl ester (5): A solution of 4-isopropyl-dihydro-furan-2-one (4.4 g, 30.9 mmol) in absolute EtOH (50 mL) is cooled to 0° C. and saturated with HBr by passing HBr gas through it for 10 minutes. The solution is warmed to room temperature and stirred for 2.5 hours. It is diluted with 150 mL of brine and extracted with Et$_2$O (3×100 mL). Drying over MgSO$_4$ followed by evaporation of the solvent gives 4.9 g (63% yield) of 3-bromomethyl-3-isobutyl-propionic acid ethyl ester as an oil. NMR (H$^1$, 300 MHz, CDCl$_3$) δ0.9 (6H, d); δ1.3 (5, m); δ1.6 (1H, m); δ2.3(1H, m); δ2.5 (1H, dd); δ3.2 (1H, dd); δ3.6 (1H, dd); δ4.1 (2H, q).

5. Preparation of 3-(Diethoxy-phosphorylmethyl)-5-methyl-hexanoic acid ethyl ester (6): 3-bromomethyl-3-isobutyl-propionic acid ethyl ester (4.6 g, 18.3 mmol) is warmed in a 170° C. oil bath under Ar. Triethyl phosphite (3.6 g, 22 mmol) is added dropwise over 2 hours. When addition is complete, the oil bath temperature is raised to 190° C. for 4 hours. The reaction mixture is cooled to room temperature, and the product is purified by MPLC in EtOAc to give 2.7 g (48% yield) of 3-(Diethoxy-phosphorylmethyl)-5-methyl-hexanoic acid ethyl ester. NMR (H$^1$, 400 MHz, CDCl$_3$) δ0.8 (6H, d); δ1.2 (5H, m); δ1.3 (6H, m); δ1.6 (1H, m); δ1.7 (1H, d); δ1.8 (1H, d); 2.3 (2H, m); δ2.5 (1H, dd); δ4.1 (6H, m).

6. Preparation of 3-(Diethoxy-phosphorylmethyl)-5-methyl-hexanoic acid (7): 3-(Diethoxy-phosphorylmethyl)-5-methyl-hexanoic acid ethyl ester (1.0 g, 3.2 mmol) and NaOH (1.8 mL, 2.0 M) are combined in 10 mL of EtOH at 0° C. After 15 minutes, the reaction mixture is warmed to room temperature and stirred overnight. The EtOH is evaporated, and 50 mL of 2.0 M NaOH is added. The solution is extracted with Et$_2$O (2×50 mL), and then acidified to pH=1 with concentrated HCl. The acidic solution is extracted with EtOAc (3×50 mL), and the combined extracts are dried over MgSO$_4$ and evaporated to give 0.65 g (72% yield) of 3-(Diethoxy-phosphorylmethyl)-5-methyl-hexanoic acid as an oil. NMR (H$^1$, 400 MHz, CDCl$_3$) δ0.9 (6H, d); δ1.3 (8H, m); δ1.6 (1H, m); δ1.8 (2H, m); δ2.3 (1H, m); δ2.5 (2H, m); δ4.1 (4H, m).

7. Preparation of [2-(Benzyloxycarbonylamino-methyl)-4-methyl-pentyl]-phosphonic acid diethyl ester (8): A solution 3-(Diethoxy-phosphorylmethyl)-5-methyl-hexanoic acid (0.65 g, 2.3 mmol), diphenyl-di-phosphoryl-azide (0.76 g, 2.8 mmol), triethyl amine (0.47 g, 4.6 mmol), and benzyl alcohol (0.5 g, 4.6 mmol) in 100 mL of toluene is warmed to reflux overnight. The toluene is evaporated, and the remaining oil is taken up in 50 mL of EtOAc. The EtOAc solution is washed with 1.0N HCl (2×50 mL), saturated NaHCO$_3$ (2×50 mL), and 50 mL of brine. Drying over Na$_2$SO$_4$ followed by evaporation of the solvent gives an oil which is purified by MPLC in EtOAc. Yield of [2-(Benzyloxycarbonylamino-methyl)-4-methyl-pentyl]-phosphonic acid diethyl ester=0.46 g (52%). NMR (H$^1$, 400 MHz, CDCl$_3$) δ0.9 (6H, m); δ1.1–1.4 (9H, m); 1.7 (2H, m); δ2.0 (1H, m); δ3.1 (1H, m); δ3.3 (1H, m); δ4.1 (4H, q); δ5.0 (2H, s); δ5.7 (1H, bs); δ7.3 (5H, m).

8. Preparation of (2-Aminomethyl-4-methyl-pentyl)-phosphonic acid (9): A solution of [2-(Benzyloxycarbonylamino-methyl)-4-methyl-pentyl]-phosphonic acid diethyl ester (0.46 g, 1.2 mmol) in 20 mL of 47% aqueous HBr is warmed at reflux overnight. The solution is cooled to room temperature, and the H$_2$O is evaporated. The remaining solid is taken up in 10 mL of H$_2$O, filtered through Celite® 545, and passed through a Dowex® 50 ion exchange column (Bed Volume=30 mL). The column is eluted with 200 mL of H$_2$O, 150 mL of 3% NH$_4$OH, and 150 mL of 10% NH$_4$OH. The basic eluates are combined and evaporated to give 0.14 g of a white solid. After drying under vacuum at 60° C. with P$_2$O$_2$, the yield of (2-Aminomethyl-4-methyl-pentyl)-phosphonic acid=0.11 g (47%). NMR (H$^1$, 400 MHz, CD$_3$OD) δ0.9 (6H, m); δ1.2 (2H, t); δ1.4 (1H, m); δ1.7 (2H, m); δ2.1 (1H, m); δ2.7 (1H, dd); δ3.0 (1H, dd). MS (m/e) 196 (M+1, 100%). Analysis for C$_7$H$_{18}$NO$_3$P: Calculated: C-43.07, H-9.29, N-7.18. Found: C-43.08, H-8.62, N-6.89.

What is claimed is:

1. The compounds of the invention are those of the formula

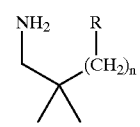

1A or a pharmaceutically acceptable salt thereof wherein:
n is an integer of from 0 to 2; and
R is a heterocycle selected from

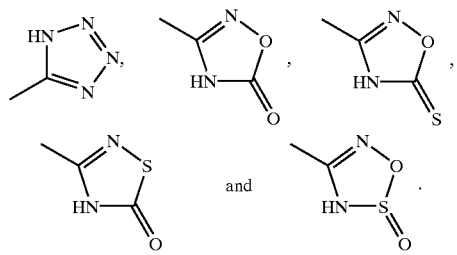

2. A compound according to claim 1 wherein n is 1 and R is

3. A compound according to claim 1 named:
4-Methyl-2-(1H-tetrazol-5-ylmethyl)-pentylamine;
3-(2-Aminomethyl-4-methyl-pentyl)-4H-[1,2,4]oxadiazole-5-thione, HCL; and
3-(2-Aminomethyl-4-methyl-pentyl)-4H-[1,2,4]oxadiazole-5-one, HCl.

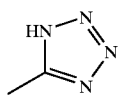 and 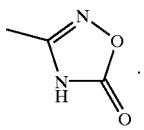

4. A pharmaceutical composition comprising a therapeutically effective amount of a compound according to claim 1 and a pharmaceutically acceptable carrier.

5. A method for treating pain comprising administering a therapeutically effective amount of a compound according to claim 1 to a mammal in need of said treatment.

* * * * *

UNITED STATES PATENT AND TRADEMARK OFFICE
CERTIFICATE OF CORRECTION

PATENT NO.   : 6,521,650 B1
DATED        : February 18, 2003
INVENTOR(S)  : Thomas Richard Belliotti et al.

It is certified that error appears in the above-identified patent and that said Letters Patent is hereby corrected as shown below:

Column 20,
Lines 41-65, should read:

1. The compounds of the invention are those of the formula

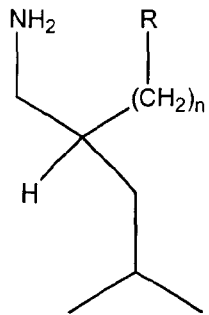

1A or a pharmaceutically acceptable salt thereof wherein:

n is an integer of from 0 to 2; and

R is a heterocycle selected from

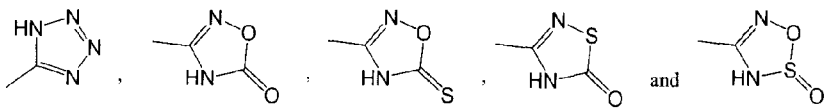

Signed and Sealed this

Fifth Day of August, 2003

JAMES E. ROGAN
*Director of the United States Patent and Trademark Office*